United States Patent [19]

L'Eplattenier et al.

[11] 3,988,323
[45] Oct. 26, 1976

[54] METAL COMPLEXES OF BISHYDRAZIDES

[75] Inventors: Francois L'Eplattenier, Therwil; Laurent Vuitel, Monthey, both of Switzerland

[73] Assignee: Ciba-Geigy Corporation, Ardsley, N.Y.

[22] Filed: Dec. 12, 1975

[21] Appl. No.: 640,374

[30] Foreign Application Priority Data
Dec. 17, 1974  Switzerland............... 16813/74

[52] U.S. Cl.................... 260/240 G; 260/438.1; 260/439 R; 260/287 R; 260/289 R; 260/288 R
[51] Int. Cl.$^2$............... C09B 55/00; C07D 215/02; C07C 119/00
[58] Field of Search.......... 260/240 G, 438.1, 439 R

[56] References Cited
UNITED STATES PATENTS

| | | | |
|---|---|---|---|
| 2,993,065 | 7/1961 | Kumins et al. | 260/439 R |
| 3,278,593 | 10/1966 | Touey et al. | 260/438.1 X |
| 3,440,254 | 4/1969 | Lenoir et al. | 260/438.1 X |
| 3,558,609 | 1/1971 | Ruckert | 260/240 G |
| 3,864,371 | 2/1975 | Inman et al. | 260/439 R |
| 3,894,083 | 7/1975 | Hofer et al. | 260/438.1 X |
| 3,939,194 | 2/1972 | Eplattenier et al. | 260/438.1 X |

*Primary Examiner*—Allen B. Curtis
*Attorney, Agent, or Firm*—Vincent J. Cavalieri

[57] ABSTRACT

1:1- and 2:1-metal complexes of bishydrazides of the formula I

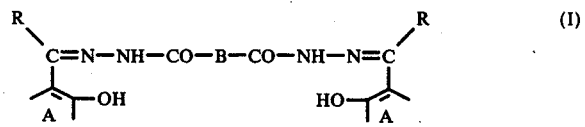

wherein both A's represent identical or different isocyclic or heterocyclic aromatic radicals, B represents an isocyclic or heterocyclic aromatic radical, and R represents hydrogen, an alkyl group containing 1 – 6 carbon atoms, or an alkyl radical, and the complexing metal ions are bivalent cations of the transition metals, zinc ions or cadmium ions which are useful for pigmenting high molecular organic material.

11 Claims, No Drawings

METAL COMPLEXES OF BISHYDRAZIDES

It has been found that new valuable 1:1- and 2:1-metal complexes of bishydrazides are obtained when a bishydrazide of the formula I

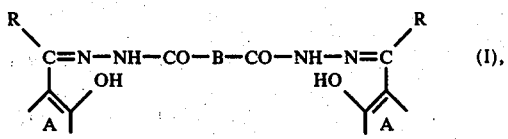

wherein both A's represent identical or different isocyclic or heterocyclic aromatic radicals, B represents an isocyclic or heterocyclic aromatic radical, and R represents hydrogen, an alkyl group containing 1 – 6 carbon atoms, or an aryl radical, is complexed with a compound which releases a bivalent transition-metal cation, a zinc or cadmium ion, in the molar ratio of 1:1 or 1:2.

Of particular interest are the metal complexes, preferably 2:1-metal complexes, of bishydrazides of the formula I wherein A represents a benzene, naphthalene, pyridine, pyrimidine, pyrazole, quinoline, isoquinolone or coumarin radical, and B represents a benzene or naphthalene radical, whereby the radical A can also be substituted by halogen atoms, hydroxy, alkyl aryl, alkoxy, nitro, cyano, carboxy, phenylazo, alkoxycarbonyl, carbamoyl or alkyl or arylcarbamoyl groups, and the radical B by halogen atoms, alkyl, aryl or alkoxy groups, R represents hydrogen or a methyl group, and the complexing compounds release bivalent ions of zinc, cobalt, nickel or copper.

Especially valuable are 2:1-metal complexes of bishydrazides of the formula II

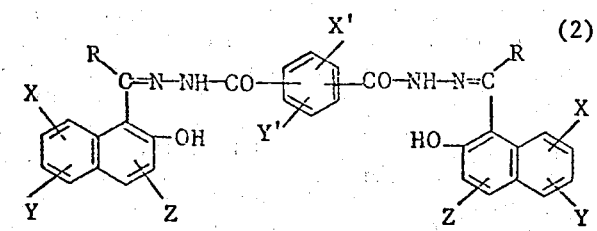

wherein X, Y and Z represent hydrogen atoms, chlorine atoms or bromine atoms, hydroxy groups, alkyl or alkoxy radicals containing 1–4 carbon atoms, nitro, cyano or carboxy radicals, carbamoyl groups or carbamoyl groups substituted by alkyl or aryl groups containing 1 – 12 carbon atoms, or alkoxycarbonyl groups containing 2 – 7 carbon atoms, X' and Y' represent hydrogen atoms or halogen atoms, alkyl or alkoxy groups containing 1 – 4 carbon atoms, or aryl groups containing 6 – 10 carbon atoms, and R represents a hydrogen atom or a methyl group, and the two carboxylic acid hydrazide radicals are bound in the para- or metaposition with respect to each other on the benzene ring.

Of special interest are the 2:1-copper-II-complexes of the aforementioned compounds, particularly the 2:1-copper-II-complex of the bishydrazide of the formula

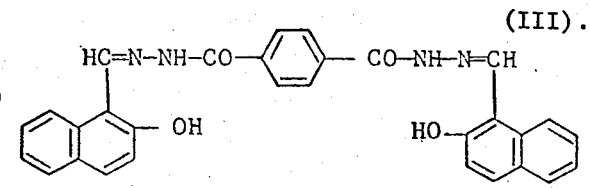

The bishydrazides of the formula I that are used as starting materials are obtained by reaction of an o-hydroxy compound of the formula

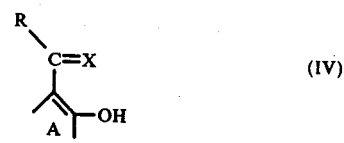

wherein X represents the group O or $NR_1$, and $R_1$ denotes an alky or aryl radical, preferably a phenyl radical, with a bishydrazide of the formula

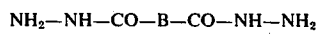

$$NH_2-NH-CO-B-CO-NH-NH_2 \quad (V)$$

wherein B has the meaning already defined.

The following may be mentioned as examples of 0-hydroxy compounds of the formula IV to be used:
salicylaldehyde,
4-chloro-2-hydroxybenzaldehyde,
5-chloro-2-hydroxybenzaldehyde,
3-nitro-2-hydroxybenzaldehyde,
5-nitro-2-hydroxybenzaldehyde,
3,5-dichloro-2-hydroxybenzaldehyde,
3,5-dibromo-2-hydroxybenzaldehyde,
5-phenylazo-2-hydroxybenzaldehyde,
5-(2'-chlorophenylazo)-2-hydroxybenzaldehyde,
5-(2',5'-dichlorophenylazo)-2-hydroxybenzaldehyde,
5-(2'-methyl-phenylazo)-2-hydroxybenzaldehyde,
5-(2'-methoxy-phenylazo)-2-hydroxybenzaldehyde,
5-(2'-methoxy-4'-nitro-phenylazo)-2-hydroxybenzaldehyde,
5-(2'-methoxy-5'-carbamoyl-phenylazo)-2-hydroxybenzaldehyde,
2-hydroxynaphthaldehyde,
6-bromo-2-hydroxynaphthaldehyde,
5-nitro-2-hydroxynaphthaldehyde,
2-hydroxy-3-carboxy-naphthaldehyde, 2-hydroxy-3-methoxycarbonyl-naphthaldehyde,
2-hydroxy-3-phenylcarbamoyl-naphthaldehyde,
2-hydroxy-3-(4'-chlorophenylcarbamoyl)-naphthaldehyde,
2-hydroxy-3-(4'-chloro-2'-methylphenylcarbamoyl)-naphthaldehyde,
2-hydroxy-3-(2',5'-dimethoxy-3'-chlorophenylcarbamoyl)-naphthaldehyde,
2-hydroxy-6-bromo-3-carboxynaphthaldehyde,
2-hydroxy-6-bromo-3-phenylcarbamoylnaphthaldehyde,
2,6-dihydroxy-4-methyl-5-cyano-3-pyridinealdehyde,
2,6-dihydroxy-4-methyl-5-carbamoyl-3-pyridinealdehyde,
2,4-dihydroxy-3-quinolinealdehyde,
5-chloro-2,4-dihydroxy-3-quinolinealdehyde,
6-chloro-2,4-dihydroxy-3-quinolinealdehyde,
7-chloro-2,4-dihydroxy-3-quinolinealdehyde,
8-chloro-2,4-dihydroxy-3-quinolinealdehyde,
6,8-dichloro-2,4-dihydroxy-3-quinolinealdehyde,
7,8-dichloro-2,4-dihydroxy-3-quinolinealdehyde,
6-methyl-2,4-dihydroxy-3-quinolinealdehyde,
7-methyl-2,4-dihydroxy-3-quinolinealdehyde,
8-methyl-2,4-dihydroxy-3-quinolinealdehyde,
6-chloro-8-methyl-2,4-dihydroxy-3-quinolinealdehyde,
2,4-dihydroxy-3-acetyl-quinoline,
2,4-dihydroxy-3-acetyl-6-methyl-quinoline,
2,4-dihydroxy-3-acetyl-6-chloroquinoline,
3-hydroxy-4-isoquinolonealdehyde,
N-methyl-3-hydroxy-4-isoquinolonealdehyde,
N-phenyl-3-hydroxy-4-isoquinolonealdehyde,
N-naphthyl-3-hydroxy-4-isoquinolonealdehyde,
2-methyl-4,6-dihydroxy-5-pyrimidinealdehyde,
2-phenyl-4,6-dihydroxy-5-pyrimidinealdehyde,
2,4,6-trihydroxy-5-pyrimidinealdehyde,
4-hydroxy-3-quinaldinealdehyde,
6-chloro-4-hydroxy-3quinaldinealdehyde,
6-methoxy-4-hydroxy-3-quinaldinealdehyde,
6-methyl-4-hydroxycoumarin-3-aldehyde,
6-chloro-4-hydroxycoumarin-3-aldehyde,
5,7-dimethyl-6-chloro-4-hydroxycoumarin-3-aldehyde,
4hydroxycoumarin-3-aldehyde,
1-phenyl-3-methyl-4-formyl-5-hydroxy-pyrazole,
1-phenyl-3-carboxy-4-formyl-5-hydroxy-pyrazole,
1-phenyl-3-carbamoyl-4-formyl-5-hydroxy-pyrazole,
1-phenyl-3-methoxycarbonyl-4-formyl-5-hydroxy-pyrazole,
1-phenyl-3-ethoxycarbonyl-4-formyl-5-hydroxy-pyrazole,
1-(2'-chlorophenyl)-3-methyl-4-formyl-5-hydroxy-pyrazole,
1-(4'-chlorophenyl)-3-methyl-4-formyl-5-hydroxy-pyrazole,
1-(2'-methylphenyl)-3-methyl-4-formyl-5-hydroxy-pyrazole,
1-(4'-methylphenyl)-3-methyl-4-formyl-5-hydroxy-pyrazole.

Instead of the aldehydes or ketones, it is also possible to use the corresponding aldimines, particularly phenylaldimines.

The following are given as examples of bishydrazides of the formula V to be used:
terephthalic acid bishydrazide,
isophthalic acid bishydrazide,
1,4-naphthylene-bis-carboxylic acid hydrazide,
1,5-naphthylene-bis-carboxylic acid hydrazide,
1,8-naphthylene-bis-carboxylic acid hydrazide,
2,6-naphthylene-bis-carboxylic acid hydrazide,
thiophene-bis-carboxylic acid hydrazide,
pyridine-bis-carboxylic acid hydrazide,
whereby the aforementioned bishydrazides can also be substituted as given above.

Examples of preferred compounds that release a bivalent metal ion are the acetate, stearate, chloride, sulphate, nitrate or phosphate of cobalt, nickel, zinc or, in particular, copper.

The complexing (metallising) of the azomethine can be performed also simulataneously with its production by condensation of the compounds of the formulae IV and V in the presence of the compound releasing the metal ion, without isolation of the ligand, preferably in a single-vessel process, in an organic solvent. The following are mentioned as solvents for the single-vessel process: methyl Cellosolve, glacial acetic acid, dimethylformamide, ethylene glycol and Carbitol.

The complexing reaction occurs at elevated temperature, preferably between 50° C and the boiling point of the employed solvent.

Since the resulting metal complexes are difficultly soluble in the solvents mentioned, they can be easily isolated by filtration. Any impurities present can be removed by washing.

The new dyestuff constitute valuable pigments that can be used in the finely divided form for the pigmenting of high-molecular organic material, e.g. cellulose ethers and cellulose esters, such as ethylcellulose, cellulose acetate, cellulose butyrate, natural resins or synthetic resins, such as polymerisation resins or condensation resins, e.g. aminoplasts, especially urea-formaldehyde resins and melamine-formaldehyde resins, alkyd resins, phenoplasts, polycarbonates, polyesters, polyamides or polyurethanes, polyolefins, such as polyethylene or polypropylene, polyvinyl chloride, polystyrene, polyacrylonitrile, polyacrylic acid esters, gum, casein, silicones and silicone resins, singly or in admixtures.

It is of no importance whether the high-molecular compounds mentioned are in the form of plastic materials or melts, or in the form of spinning solutions, lacquers, coating materials or printing inks or pastes. Depending on the purpose of application, it proves advantageous to use the new pigments as toners or in the form of preparations. The preparations can contain, in addition to the pure pigment, for example natural resins such as abietic acid or esters thereof, ethylcellulose, cellulose acetobutyrate, alkaline-earth salts of higher fatty acids, fatty amines such as stearylamine or rosin amine, vinyl chloride/vinyl acetate copolymers, polyacrylonitrile or polyterpene resins, or water-soluble dyestuffs, for example dyestuff sulphonic acids or the alkaline-earth salts thereof.

The dyestuffs obtained are characterised by high tinctorial strength and good general fastness properties, especially fastness to light, weather and migration.

In the following Examples, except where otherwise stated, parts denote parts by weight and percentages per cent by weight, and temperatures are given in degrees Centigrade.

EXAMPLE 1

A. Production of the ligands 10.33 parts of 2-hydroxy-1-naphthaldehyde and 5.82 parts of terephthalic acid bishydrazide are stirred in 200 parts by volume of glacial acetic acid for 2 hours at 100°. The reaction product is filtered off at 80°, subsequently well washed with glacial acetic acid and alcohol and dried at 80° in vacuo. There are obtained 14.5 parts (96% of theory) of a yellowish powder of the formula

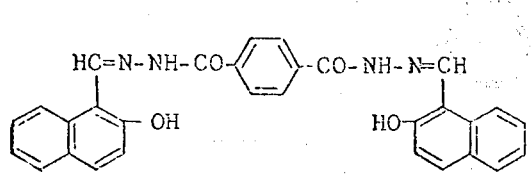

| Microanalysis: | % | C | H | N |
|---|---|---|---|---|
| calculated: | | 71.70 | 4.41 | 11.14 |
| found: | | 71.4 | 4.6 | 11.2 |

-continued

The bishydrazides in Table 1 are synthesised in an analogous manner. The given yields are yields of analytically pure compounds of the general formula

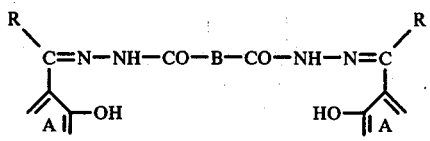

| Example No. | R | A | B | Yield |
|---|---|---|---|---|
| 2 | H | 2,4-dichloro-6-methylphenol | para-phenylene | 96% |
| 3 | H | 3-hydroxy-1-methyl-2-naphthoic acid | " | 98% |
| 4 | H | 3-hydroxy-1-methyl-N-phenyl-2-naphthamide | " | 75% |
| 5 | H | 2,4-dihydroxy-3-methylquinoline | " | 97% |
| 6 | H | 2-hydroxy-1-methylnaphthalene | meta-phenylene | 100% |
| 7 | H | 3-hydroxy-1-methyl-2-naphthoic acid | " | 93% |
| 8 | H | 3-hydroxy-1-methyl-N-(4-chlorophenyl)-2-naphthamide | para-phenylene | 98% |
| 9 | H | 2,4-dichloro-6-methylphenol | meta-phenylene | 63% |

-continued

| Example No. | R | A | B | Yield |
|---|---|---|---|---|
| 10 | H | H₃C group with N-N-phenyl hydrazone and OH (acetylacetone phenylhydrazone derivative) | 1,4-phenylene | 89% |
| 11 | H | " | 1,3-phenylene | 86% |
| 12 | H | o-cresol (2-methylphenol) | 1,4-phenylene | 98% |
| 13 | CH₃ | " | " | 65% |
| 14 | H | 3-hydroxy-4-methyl-N-phenyl-2-naphthamide | 1,3-phenylene | 91% |
| 15 | H | 1-methyl-2-naphthol | 2,5-thienylene | 94% |
| 16 | phenyl (tolyl) | 4-hydroxy-3-methylquinolin-2-ol | 2,5-thienylene | 55% |
| 17 | CH₃ | 4-hydroxy-3-methylquinolin-2-ol | 2,5-thienylene | 50% |
| 18 | H | 4-hydroxy-3-methylquinolin-2-ol | 2,5-thienylene | 100% |
| 19 | phenyl (tolyl) | 4-hydroxy-3-methylquinolin-2-ol | 1,4-phenylene | 51% |
| 20 | CH₃ | 4-hydroxy-3-methylquinolin-2-ol | 1,4-phenylene | 54% |

EXAMPLE 21

B. Production of the metal complexes 2.01 parts of the ligand from Example 1 are reacted in 50 parts by volume of methyl Cellosolve with 1.6 parts of $Cu(CH_3COO)_2 \cdot H_2O$ for 3 hours at 100°. The olive green metal complex is filtered off at room temperature; it is then well washed with alcohol, water and acetone and dried at 80° in vacuo. There are obtained 2.3 parts (92% of theory) of a compound of the composition $C_{30}H_{18}Cu_2N_4O_4$, which corresponds to a 2:1 $Cu^{2+}$-complex of the ligand from Example 1.

EXAMPLE 22

If the procedure is carried out as in Example 21 but with only half the amount of $Cu(CH_3COO)_2 \cdot H_2O$, i.e. 0.8 part, then there are obtained 2.0 parts (89% of theory) of a compound of the composition $C_{30}H_{20}CuN_4O_4$, which corresponds to a 1:1 $Cu^{2+}$-complex of the ligand from Example 1.

The metal complexes given in Table 2 are produced by a procedure analogous to that of Examples 21 and 22.

TABLE 2

| Ex. No. | Complexing agent from Ex. No. | Metal complex $M^{2+}$ 1:1 | Metal complex $M^{2+}$ 2:1 | yield | shade in PVC |
|---|---|---|---|---|---|
| 23 | 1 | Ni | — | 100% | brown-yellow |
| 24 | 3 | Ni | — | 97% | yellow |
| 25 | 3 | Cu | — | 66% | yellow |
| 26 | 3 | — | Cu | 98% | yellow |
| 27 | 2 | Cd | — | 76% | yellow |
| 28 | 2 | Ni | — | 100% | yellow |
| 29 | 5 | Ni | — | 100% | yellow |
| 30 | 5 | Cu | — | 100% | green-yellow |
| 31 | 9 | Ni | — | 50% | yellow |
| 32 | 9 | — | Cu | 80% | green-yellow |
| 33 | 6 | Ni | — | 83% | yellow |
| 34 | 6 | — | Cu | 85% | green-yellow |
| 35 | 7 | Ni | — | 92% | yellow |
| 36 | 7 | Cu | — | 79% | yellow |
| 37 | 1 | Co | — | 100% | brown |
| 38 | 3 | Co | — | 97% | brown-yellow |
| 39 | 4 | Ni | — | 88% | yellow-orange |
| 40 | 4 | — | Cu | 98% | brown-yellow |
| 41 | 5 | — | Cu | 91% | green-yellow |
| 42 | 8 | Ni | — | 80% | yellow-orange |
| 43 | 1 | — | Zn | 100% | yellow |
| 44 | 12 | Ni | — | 100% | yellow |
| 45 | 12 | — | Cu | 73% | green-yellow |
| 46 | 11 | Ni | — | 77% | yellow |
| 47 | 11 | Cu | — | 50% | green-yellow |
| 48 | 11 | — | Cu | 65% | green-yellow |
| 49 | 13 | Ni | — | 85% | yellow |
| 50 | 13 | — | Cu | 93% | green-yellow |
| 51 | 14 | — | Cu | 93% | yellow |
| 52 | 15 | — | Cu | 100% | brown |
| 53 | 16 | — | Cu | 100% | green-brown |
| 54 | 17 | — | Cu | 100% | green-brown |
| 55 | 18 | — | Cu | 100% | green-brown |
| 56 | 19 | — | Cu | 100% | green-yellow |
| 57 | 20 | — | Cu | 100% | green-yellow |

We claim:

1. 1:1- and 2:1-metal complexes of bishydrazides of the formula I

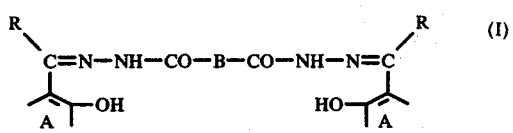

wherein A represents a hydrocarbon radical selected from the group consisting of benzene or naphthalene or a heterocyclic radical selected from the group consisting of pyridine, pyrimidine, pyrazole, quinoline, isoquinoline or coumarin, and B represents a benzene or naphthalene radical, whereby the radical A can also be substituted by halogen atoms, hydroxy, alkyl, aryl, alkoxy, nitro, cyano, carboxy, alkoxycarbonyl, carbamoyl or alkyl or aryl carbamoyl groups, and the radical B by halogen atoms, alkyl, aryl or alkoxy groups, R represents a hydrogen atom where A is a heterocyclic radical or a hydrogen atom or methyl group where A is a hydrocarbon radical, and the complexing metal ions are bivalent ions of zinc, cobalt, nickel or copper.

2. Metal complexes according to the claim 1, characterised in that A represents a naphthalene or quinoline radical, and B represents a p-phenylene radical.

3. 2:1-Metal complexes according to the claim 1, characterised by a bishydrazide of the formula I.

4. 2:1-Copper-II-complexes according to the claim 1, characterised by a bishydrazide of the formula I.

5. Metal complexes according to claim 1, characterised by a bishydrazide of the formula II

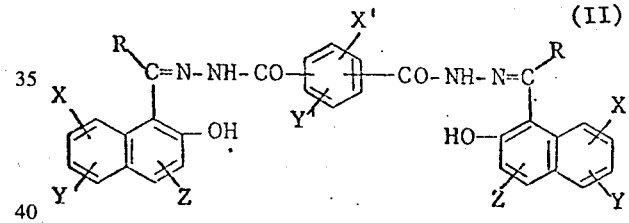

wherein X, Y and Z represent hydrogen atoms, chlorine atoms or bromine atoms, hydroxy groups, alkyl or alkoxy radicals containing 1 to 4 carbon atoms, cyano or carboxy radicals, carbamoyl groups or carbamoyl groups substituted by alkyl or aryl groups containing 1 – 12 carbon atoms, or alkoxy carbonyl groups containing 2 – 7 carbon atoms, X' and Y' represent hydrogen atoms or halogen atoms, alkyl or alkoxy groups containing 1 – 4 carbon atoms, or aryl groups containing 6 – 10 carbon atoms, and R represents a hydrogen atom or a methyl group, and the two carboxylic acid hydrazide radicals are bound in the para- or meta-position with respect to each other on the benzene ring.

6. 2:1-Metal complexes according to the claim 5, characterised by a bishydrazide of the formula II.

7. 2:1-Copper-II-complexes according to the claim 5, characterised by a bishydrazide of the formula II.

8. 2:1-Copper-II-complex according to the claim 5, characterised by a bishydrazide of the formula III 9. 1:1-Nickel complex according to the claim 5, characterised by a bishydrazide of the formula III
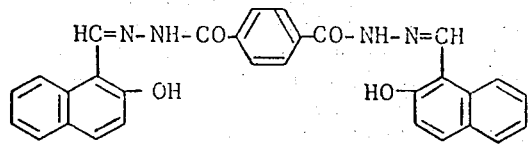
(III).
10. 1:1-Nickel complex according to the claim 1, characterised by a bishydrazide of the formula
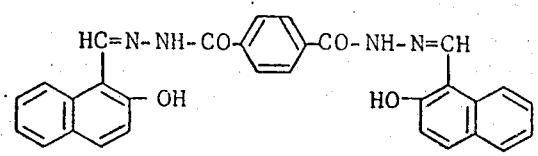
(III).
11. 1:1-Copper-II-complex according to the claim 1, characterised by a bishydrazide of the formula
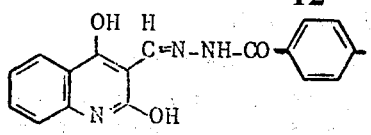
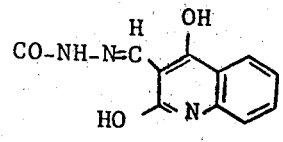
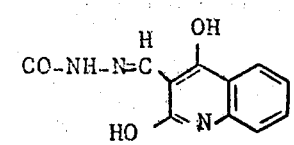
* * * * *